United States Patent
Nagoshi et al.

(10) Patent No.: US 6,867,417 B2
(45) Date of Patent: Mar. 15, 2005

(54) METHOD OF ACQUIRING DATA FROM MULTI-ELEMENT DETECTOR IN INFRARED IMAGING APPARATUS

(75) Inventors: Toshiyuki Nagoshi, Hachioji (JP);
Seiichi Kashiwabara, Hachioji (JP);
Jun Koshoubu, Hachioji (JP)

(73) Assignee: Jasco Corporation, Tokyo (JP)

( * ) Notice: Subject to any disclaimer, the term of this patent is extended or adjusted under 35 U.S.C. 154(b) by 187 days.

(21) Appl. No.: 10/355,030

(22) Filed: Jan. 31, 2003

(65) Prior Publication Data

US 2003/0149532 A1 Aug. 7, 2003

(30) Foreign Application Priority Data

Feb. 4, 2002 (JP) ........................................ 2002-026992

(51) Int. Cl.[7] ................................................. G01J 5/02
(52) U.S. Cl. ............................ 250/339.08; 250/339.07; 250/339.06
(58) Field of Search ...................... 250/339.08, 339.07, 250/339.06, 339.01, 338.1, 336.1

(56) References Cited

U.S. PATENT DOCUMENTS 6,025,913 A * 2/2000 Curbelo ...................... 356/453
2003/0057374 A1 * 3/2003 Schuebel et al. ......... 250/339.08
2003/0146386 A1 * 8/2003 Nagoshi et al. .......... 250/339.08
2003/0197800 A1 * 10/2003 Petrick et al. ............... 348/308
2004/0032581 A1 * 2/2004 Nikoonahad et al. .... 356/237.2
2004/0174959 A1 * 9/2004 Green ........................... 378/146

* cited by examiner

*Primary Examiner*—David Porta
*Assistant Examiner*—Christine Sung
(74) *Attorney, Agent, or Firm*—Oliff & Berridge, PLC

(57) ABSTRACT

It is an object of the present invention to provide a data acquiring method in an infrared imaging apparatus comprising an FTIR device of a continuous scan type for detecting a signal by a multi-element detector. A method of acquiring data from a multi-element detector in an infrared imaging apparatus comprising the steps of scanning each element of the multi-element detector in order synchronously with a sampling signal (12) generated by a reference signal (10) of an interferometer and repeating a series of scanning operations after completely scanning all the elements, thereby carrying out scan, shifting a starting point of sampling in next scan by one element from the starting point of the previous scan, thereby carrying out the same scanning, and repeating the scan at the number of times corresponding to the number of all the elements and then extracting data for each element from storing sampling data, thereby acquiring a data sequence of all the sampling points for each element.

2 Claims, 5 Drawing Sheets

The first scanning

The second scanning

The third scanning

Repeating the scanning 64×64 times

METHOD OF ACQUIRING DATA FROM MULTI-ELEMENT DETECTOR IN INFRARED IMAGING APPARATUS

RELATED APPLICATIONS

This application claims priority to the Japanese Patent Application No. 2002-26992 filed on Feb. 4, 2002 and is hereby incorporated with reference for all purposes.

BACKGROUND OF THE INVENTION

1. Field of the Invention

The present invention relates to a method of acquiring data from a multi-element detector in an infrared imaging apparatus, and more particularly to an improvement in a method of acquiring data from a multi-element detector in the case in which a Fourier transform infrared spectroscopic device of a continuous scan type is used.

2. Prior Art

A multi-element detector using an MCT or an InSb is referred to as a Focal Plane Array (FPA) detector, and has a mechanism for scanning a photoelectric output from each element arranged one-dimensionally or two-dimensionally and is utilized for a detecting device of an infrared imaging apparatus.

In an infrared imaging apparatus comprising a Fourier transform infrared spectroscopic (FTIR) device for detecting a signal by means of the FPA detector, a light incident from a light source of the FTIR device becomes interferogram by an interferometer and is irradiated onto a sample. The light transmitted through the sample is photoelectrically converted by an FPA detector and thus generates an analog electric signal. The analog electric signal is converted into a digital signal by an A/D converter and is then transmitted to a computer, and is stored as digital data in a memory. The data are subjected to an arithmetic processing by a CPU and an infrared image of the sample is then displayed on the display based on image data obtained finally.

By using a Fourier transform infrared spectroscopic (FTIR) device of a step scan type as an infrared imaging apparatus, for example, it is possible to scan all elements at an optional scanning speed in each step to obtain data.

In the infrared imaging apparatus comprising the FTIR device for detecting a signal by a multi-element detector, however, there is a problem in that the FTIR device of a step scan type is expensive. Consequently, it has been desired that a more inexpensive continuous scan type should be used. For this reason, it has been desirable to obtain a method of acquiring data from an FPA detector when an FTIR device system of a continuous scan type is applied.

SUMMARY OF THE INVENTION

The present invention has an object to provide a data acquiring method in an infrared imaging apparatus comprising an FTIR device of a continuous scan type for detecting a signal by a multi-element detector.

The present invention provides a method of acquiring data from a multi-element detector in an infrared imaging apparatus comprising a Fourier transform infrared spectroscopic device of a continuous scan type for detecting a signal by the multi-element detector, comprising the steps of:

scanning each element of the multi-element detector in order synchronously with a sampling signal generated by a reference signal of an interferometer and repeating the series of scanning operations after completely scanning all the elements, thereby carry out scan;

shifting a starting point of the sampling in next scan by one element from the starting point of the previous scan, thereby carrying out the same scanning; and repeating the scan at the number of times corresponding to the number of all the elements and then extracting data for each element from storing sampling data, thereby acquiring a data sequence of all the sampling points for each element.

DETAILED DESCRIPTION OF THE PREFERRED EMBODIMENT

An embodiment of the present invention will be described below with reference to the drawings.

Figure 6:
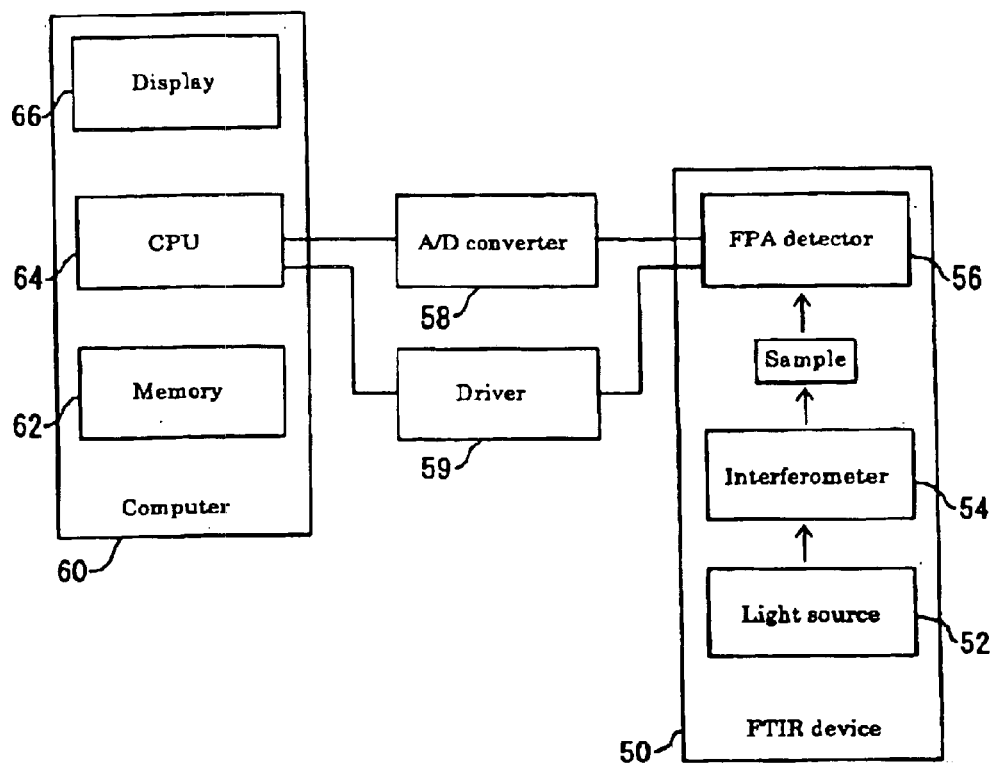
FIG. 6 is an explanatory diagram schematically showing the signal path of the infrared imaging apparatus.

FIG. 6 schematically shows the signal path of an infrared imaging apparatus comprising a Fourier transform infrared spectroscopic (FTIR) device for detecting a signal by means of the FPA detector. In FIG. 6, a light incident from a light source 52 of the FTIR device 50 becomes interferogram by an interferometer 54 and is irradiated onto a sample. The light transmitted through the sample is photoelectrically converted by an FPA detector 56 and thus generates an analog electric signal. The analog electric signal is converted into a digital signal by an A/D converter 58 and is then transmitted to a computer 60, and is stored as digital data in a memory 62. There is provided a driver circuit 59 for controlling the A/D conversion of a measurement value for any element in the FPA detector 56 in response to a signal sent from a CPU. The driver 59 selects signal of which element in FPA detector 59 to be converted into digital data. The data are subjected to an arithmetic processing by arithmetic unit 64 such as a CPU and an infrared image of the sample is then displayed on the display 66 based on image data obtained finally.

In an FTIR device of a continuous scan type, an interference signal of a laser modulated with the movement of a movable mirror that an interferometer provides with is used as a reference signal in order to accurately locate the position of the movable mirror, and the output of a detector is sampled synchronously with a sampling signal based on the reference signal.

Figure 7:
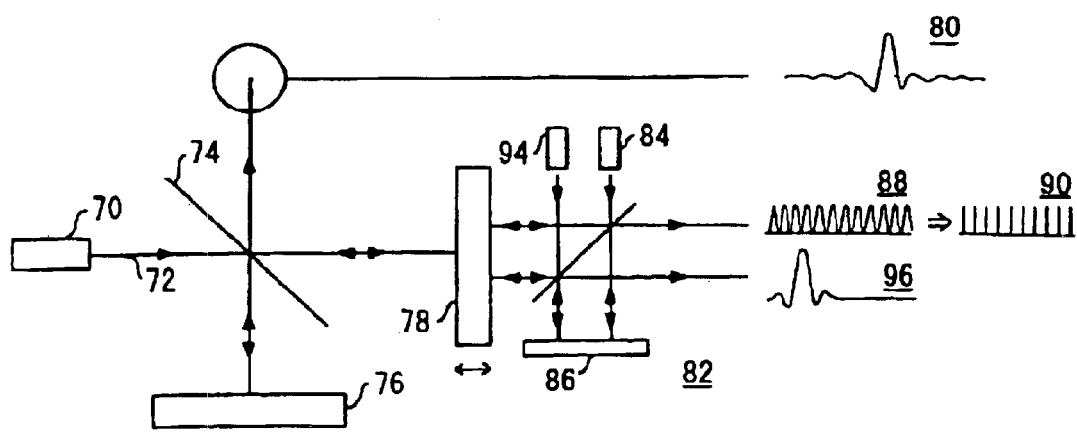
FIG. 7 is an explanatory diagram schematically showing the structure of an interferometer.

FIG. 7 shows an example of the structure of the interferometer provided in the FTIR device of a continuous scan type. An infrared light 72 emitted from a light source 70 is divided into a fixed mirror 76 direction and a movable mirror 78 direction by a beam splitter 74. Lights reflected by the fixed mirror 76 and the movable mirror 78 are superposed again by the beam splitter 74 so that an interference light 80 (interferogram) is generated by an optical path difference corresponding to the position of the movable mirror 78 moving at a constant speed.

On the other hand, there is provided an interferometer 82 referred to as a subinterferometer for correlating the sampling of the interference light 80 transmitted through the sample and the optical path difference. A monochromatic light 84 of a He—Ne laser or the like is introduced into the interferometer 82 so that an interference light 88 is generated by an optical path difference between the fixed mirror 86 and the movable mirror 78. The interference light 88 is based on the monochromatic light and a detected signal of the interference light 88 is therefore sine wave-shaped. A detected electric signal is converted into a comb-shaped signal 90 shown in FIG. 7, for example, and a signal indicative of sampling is obtained so that the said optical path difference can be specified during the sampling. Moreover, a white light 94 is also introduced into the interferometer 82. Consequently, a point at which the intensity of an interference light is a maximum can be set to be the reference of a position as a position where the optical path difference is zero.

In an FTIR device of a continuous scan type, the interference signal of a laser which is modulated by driving a movable mirror including an interferometer is used as a reference signal in order to accurately locate the position of the movable mirror as described above. In the case in which a detector having a single element is used, the output of a detector is sampled synchronously with a sampling signal based on the reference signal, thereby correlating a sampling point with the position of the movable position.

On the other hand, an FPA detector has a mechanism for scanning each element by the driver as a switching circuit to detect a signal. More specifically, in case of a element array illustrated in FIG. 1, for example, (1, 1), (1, 2) . . . (1, 64) are scanned for the elements on a first row in order, (2, 1), (2, 2) . . . (2, 64) are then scanned for the elements on a second row in order, and each element on 3 to 64 rows are scanned in order in the same manner.

Figure 1:
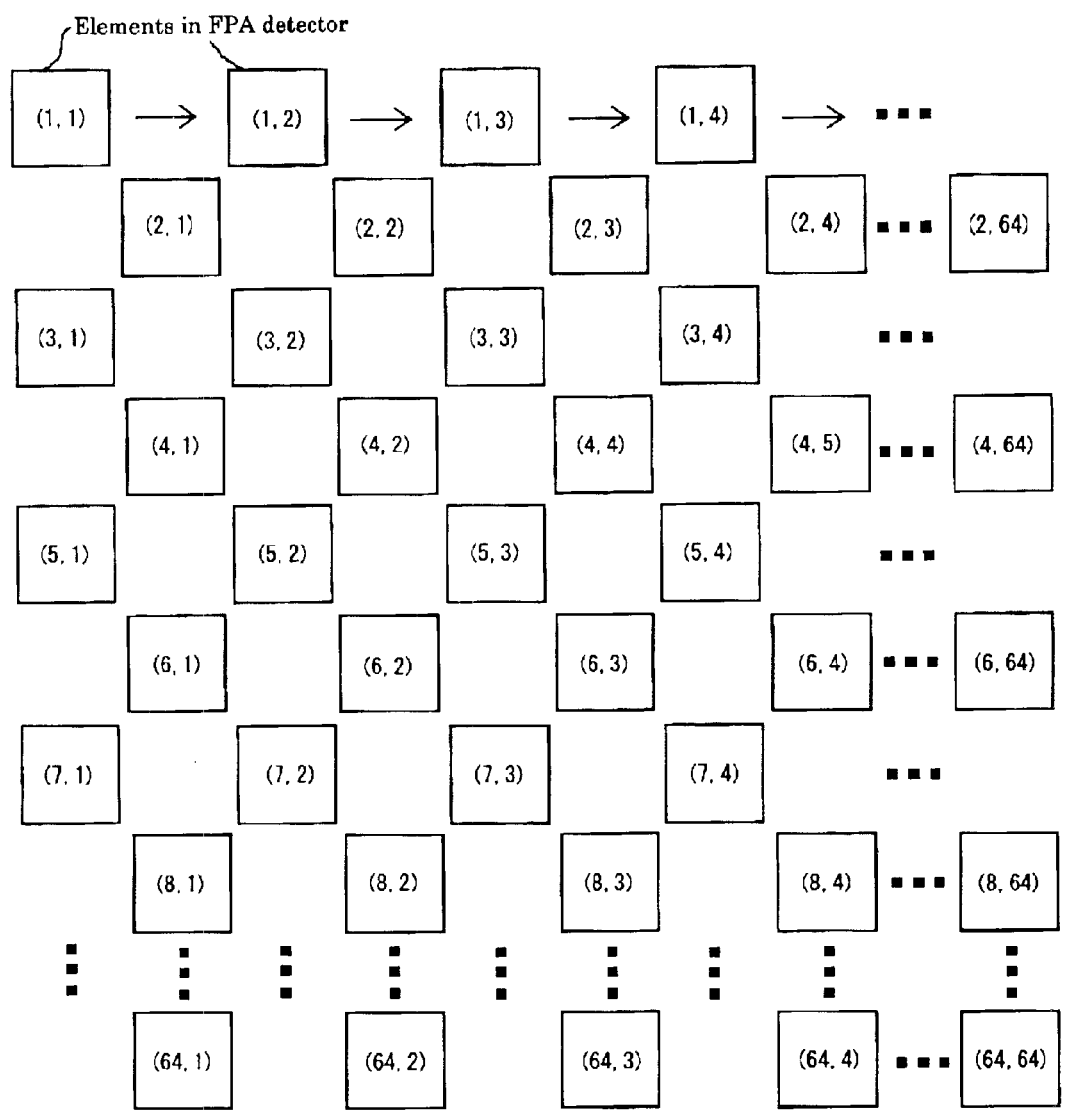
FIG. 1 is a schematic diagram showing an example of the element array of an FPA detector.
Figure 2:
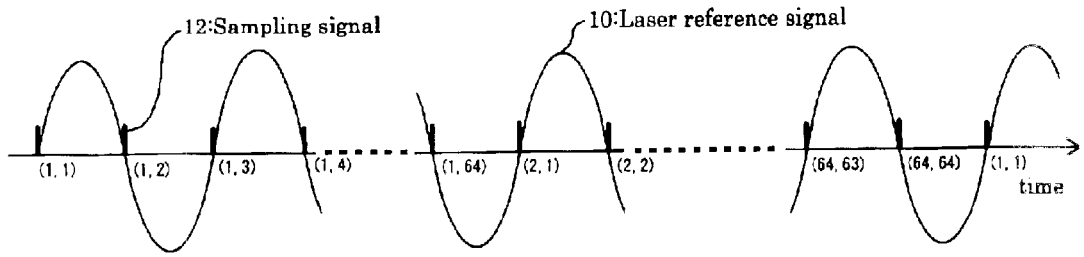
FIG. 2 is an explanatory diagram showing a method according to the present invention.
Figure 2:
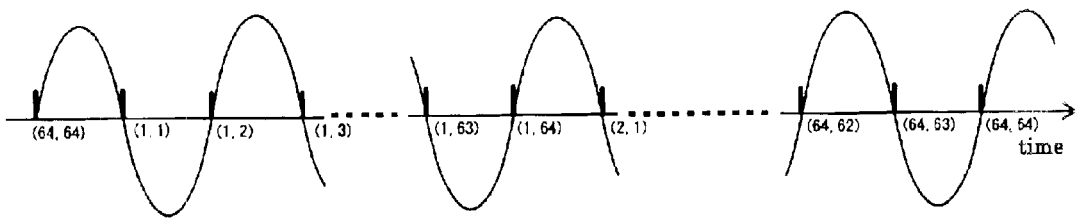
Figure 2:
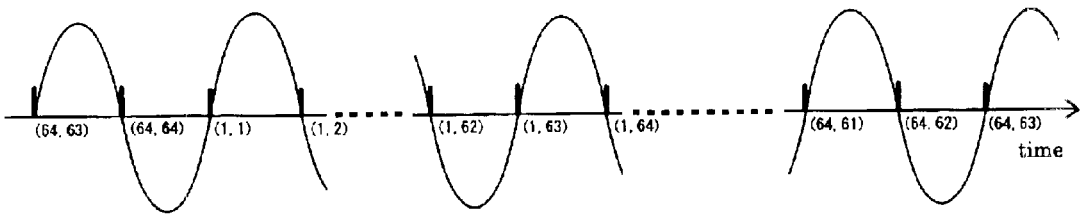
Figure 2:

Therefore, the present inventors vigorously investigated a method of acquiring data from a detector based on the sampling principle of an FTIR device of a continuous scan type and the scanning mechanism provided in the FPA detector, and found the following method as a result of the investigations. FIG. 2 schematically shows the acquisition of data from a detector according to the method of the present invention by taking, as an example, the case in which the FPA detector of FIG. 1 is used. In FIG. 2, a laser reference signal 10 generates a sampling signal 12 in KHz order (from several hundreds Hz to several thousands KHz) corresponding to the position of the movable mirror of an interferometer.

In the present invention, each element is scanned one by one in order synchronously with the sampling signal 12 generated from the laser reference signal 10 of the interferometer as shown in FIG. 2. More specifically, (1, 1), (1, 2) . . . (64, 64) are scanned in order of each sampling signal as described above.

When the element of (64, 64) is completely scanned, the scanning is repeated in the same manner at a next sampling signal from (1, 1) to (64, 64). Thus, a series of scanning operations are repeated and the scanning is thus carried out throughout all sampling points.

In the next scan, the starting point of sampling is shifted by one element from the starting point of previous scan and the same scan as described above is carried out. Consequently, data having sampling points shifted by one from the previous scan are obtained for each element.

By thus repeating each scan for shifting the sampling point by one from the previous scan to carry out the same scanning as described above at the number of times corresponding to the number of all elements (64×64), data on all the sampling points can be obtained for each element.

The sampling data of all scanning operations are stored in a memory. The data for each element are extracted from the memory and are reconstructed by an arithmetic unit, for example, a CPU as a data sequence of all the sampling points for each element.

Figures 3, 4:
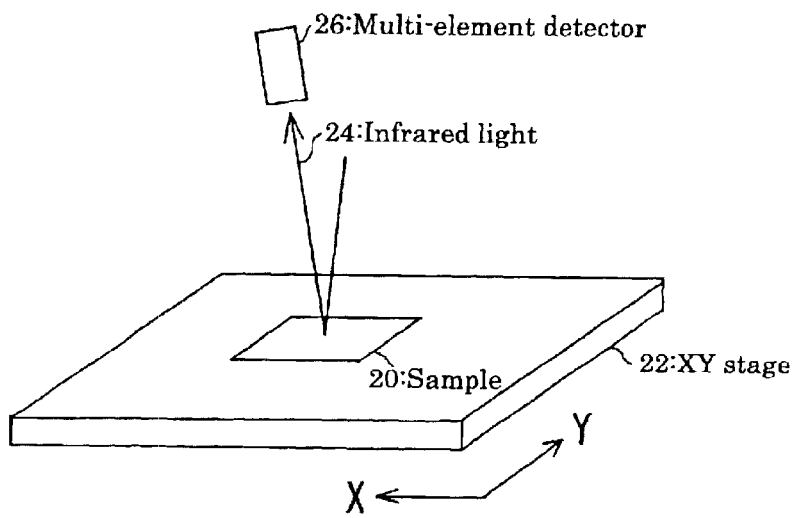
FIG. 3 is an explanatory diagram showing the method according to the present invention.
FIG. 4 is a view showing a measuring mechanism to which a method for enhancing an image resolution is applied in a method of acquiring data from a multi-element detector in an infrared imaging apparatus comprising a Fourier transform infrared spectroscopic device for detecting a signal by a multi-element detector.

More specifically, as shown in FIG. 3, sampling data obtained at intervals by each scan for a element of (1, 1) are extracted, for example, and are reconstructed as a data sequence in order of the sampling point. Consequently, the data sequence of all the sampling points are obtained for the element of (1, 1). Thus, the data sequence of all the sampling points is obtained for all the elements.

The present inventors found that the following method can be applied to a method of acquiring data from a multi-element detector when obtaining an infrared image by using an FPA detector for the detector of an FTIR device. This method will be described below.

As illustrated in FIG. 1, a space having no element is provided between the elements of the FPA detector and measuring information corresponding to the space cannot be obtained.

Accordingly, image information about a clearance between the elements cannot be obtained and an image resolution has a constant limit. Furthermore, if the image information about the clearance between the elements can be obtained, there is a possibility that more detailed information can be extracted from an image thus obtained.

Consequently, investigations were made in order to more enhance an image resolution when obtaining an infrared image by using the FPA detector. As a result, there was found a method of acquiring data from a multi-element detector in an infrared imaging apparatus including a Fourier transform infrared spectroscopic device for detecting a signal by a multi-element detector characterized by fixing an XY stage having a sample mounted thereon to carry out the first measurement, thereby acquiring data from the multi-element detector; and moving the XY stage to shift a position on the measured surface of a sample detected by each element of the multi-element detector to carry out next measurement, acquiring complement data by repeating one or plural operations.

The above method will be described below.

FIG. 4 shows an example of a measuring mechanism to which the above method is applied. As shown in FIG. 4, a sample 20 is mounted on an XY stage 22 and an infrared light 24 irradiated on the sample is detected by a fixed multi-element detector 26. As described above, the element array of the multi-element detector 26 has a clearance between the elements. Therefore, image information about that portion cannot be obtained and an image resolution has a limit.

Therefore, the present inventors made investigations in order to solve the problem and found that the problem can be solved by the following method as a result of the investigations. The XY stage 22 mounting the sample 20 thereon is fixed to carry out the first measurement so that data are acquired from the multi-element detector.

In order to acquire data on a clearance portion other than a measuring range on the measured surface of the sample 20 corresponding to each element which cannot be obtained by the first measurement, the XY stage 22 is moved to shift a position on the measured surface of the sample 20 which is detected by each element of the multi-element detector 26, thereby carrying out next measurement to acquire complement data.

Figure 5:
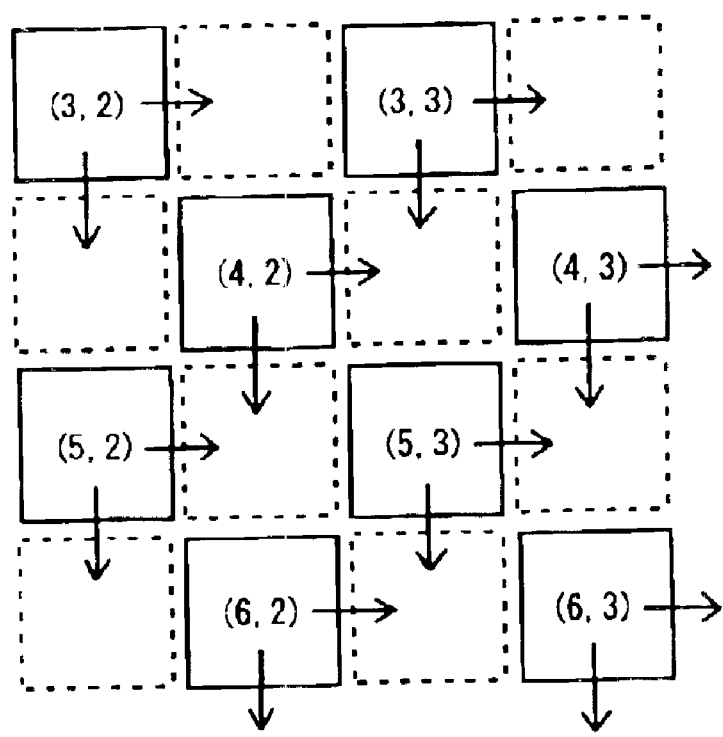
FIG. 5 is a schematic diagram illustrating a method for enhancing an image resolution in the method of acquiring data from the multi-element detector in the infrared imaging apparatus comprising the Fourier transform infrared spectroscopic device for detecting a signal by the multi-element detector.

The foregoing will be described with reference to FIG. 5 by extracting a part of the element array in FIG. 1. The XY stage is moved by approximately half of an element pitch width in a direction of an arrow. For next measurement, consequently, the measuring range on the measured surface of the sample 20 corresponding to each element corresponds to the clearance portion at time of the first measurement. Thus, it is possible to obtain data in a portion which cannot be obtained in the previous measurement.

Thus, both the data obtained in the first measurement and the complement data obtained in the next measurement are set to be image data and an image can be obtained based thereon. Consequently, an image resolution can be enhanced.

The clearance between the elements of the detector is varied according to circumstances. In the case in which the clearance is large, therefore, the XY stage is moved for each measurement to carry out the measurement for obtaining the complement data plural times. Thus, the resolution can be enhanced.

According to the method described above, it is possible to produce an advantage that the image resolution can be enhanced.

As described above, according to the present invention, there is provided a data acquiring method in an infrared imaging apparatus comprising an FTIR device of a continuous scan type for detecting a signal by a multi-element detector.

What is claimed is:

1. A method of acquiring data from a multi-element detector in an infrared imaging apparatus comprising a Fourier transform infrared spectroscopic device of a continuous scan type for detecting a signal by the multi-element detector, comprising the steps of:

scanning each element of the multi-element detector in order synchronously with a sampling signal generated by a reference signal of an interferometer and repeating a series of scanning operations after completely scanning all the elements, thereby carrying out the scan;

shifting a starting point of sampling in a next scan by one element from the starting point of the previous scan, and carrying out the scanning; and repeating the scan at the number of times corresponding to the number of all the elements and then extracting data for each element from stored sampling data, thereby acquiring a data sequence of all sampling points for each element.

2. The method of claim 1 wherein the sampling data of all scanning operation is stored in a memory.

* * * * *